United States Patent [19]
Simpson

[11] 3,954,987
[45] May 4, 1976

[54] 2-ALKYL-4-SUBSTITUTED AMINO-QUINAZOLINES AND NITRATES THEREOF IN THE TREATMENT OF MYOCARDIAL SHOCK
[75] Inventor: William R. Simpson, Mendham, N.J.
[73] Assignee: Sandoz, Inc., E. Hanover, N.J.
[22] Filed: Dec. 3, 1974
[21] Appl. No.: 529,025

Related U.S. Application Data
[60] Division of Ser. No. 317,545, Dec. 22, 1972, Pat. No. 3,867,387, which is a continuation-in-part of Ser. No. 212,784, Dec. 27, 1971, abandoned.

[52] U.S. Cl. .............................................. 424/251
[51] Int. Cl.² ........................................ A61K 31/505
[58] Field of Search .................................. 424/251

[56] References Cited
UNITED STATES PATENTS
3,449,498   6/1969   DeStevens et al. ................. 424/251
3,517,005   6/1970   Cronin et al. ....................... 424/251
3,637,699   1/1972   Gabel et al. ................. 260/256.4 Q
3,637,700   1/1972   Gabel et al. ................. 260/256.4 Q
3,637,701   1/1972   Gabel et al. ................. 260/256.4 Q Primary Examiner—Stanley J. Friedman
Attorney, Agent, or Firm—Gerald D. Sharkin; Richard E. Vila

[57]   ABSTRACT

Disclosed are compounds of the class of quinazolines substituted at the 2-position by lower alkyl and at the 4-position by an amino function bearing a hydroxyalkyl nitrate moiety, e.g., 4-(5-hydroxypentyl) amino-2-methyl-6,7-dimethoxy-quinazoline nitrate. The compounds and their corresponding hydroxy intermediates have various pharmacological activities in animals and are useful, for example, as anti-anginal agents and as agents in the treatment of shock.

5 Claims, No Drawings

2-ALKYL-4-SUBSTITUTED AMINO-QUINAZOLINES AND NITRATES THEREOF IN THE TREATMENT OF MYOCARDIAL SHOCK

This application is a division of application Serial No. 317,545, filed Dec. 22, 1972 and now U.S. Letters Pat. No. 3,867,387, which application is a continuation-in-part of application Serial No. 212,784, filed Dec. 27, 1971, now abandoned.

This invention relates to quinazoline derivatives, and more particularly to quinazolines which are substituted at the 2-position by lower alkyl and at the 4-position by an amino function bearing a hydroxyalkyl nitrate moiety. The invention also relates to pharmaceutical methods and compositions utilizing said compounds. The invention further relates to certain corresponding hydroxyalkyl substituted quinazolines useful as intermediates in preparation of said nitrates and also useful per se as pharmaceutically active substances.

In prior applications of myself and Lloyd P. Gabel, resulting in U.S. Letters Pat. Nos. 3,637,699, 3,637,700 and 3,637,701, there are described certain quinazolines substituted at the 4-position by a moiety containing a 4-amino function bearing a hydroxyalkyl nitrate group, such compounds being useful, for example, as coronary dilators and antianginal agents, and suitably prepared from their corresponding hydroxy intermediates which also possess hypotensive and coronary dilator activity.

The compounds of the invention may be represented by the structural formula I:

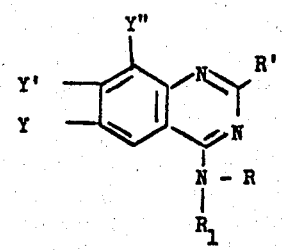

wherein
R' is lower alkyl of 1 to 4 carbon atoms,
R is from the group of
  a. $-CH_2(-CH_2)_n-ONO_2$ b. $-CH_2(-\overset{R}{\underset{|}{C}H})_n-ONO_2$, and c. $-CH_2(-CH_2)_z-N[-CH_2(CH_2)_y-ONO_2]_2$ $R_1$ is from the group of
  d. $-CH_2(-CH_2)_n-ONO_2$ when R is a) as above defined,
  e. hydrogen, and
  f. lower alkyl of 1 to 4 carbon atoms, $R^0$ is hydrogen, $-(CH_2-)_mCH_3$ or $-(CH_2-)_nONO_2$, provided that one $R^0$ (and only one) is other than hydrogen, that the sum of n and m does not exceed 6 and that the sum of n and y does not exceed 7, or R and $R_1$ together with the 4-amino nitrogen attached to the quinazoline ring form

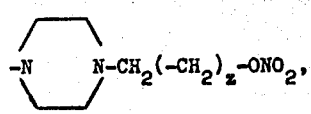

n is 1 to 6, preferably 3 to 5,
m is 0 to 4,
y is 1 to 4,
z is 1 to 4, and
each of Y, Y' and Y'' is hydrogen, lower alkoxy of 1 to 3 carbon atoms, e.g., methoxy or lower alkyl of 1 to 3 carbon atoms, e.g. methyl, or Y and Y' together form methylenedioxy (with Y'' being hydrogen); provided that no more than 2 of Y, Y' and Y'' are lower alkyl; or a pharmaceutically acceptable non-toxic acid addition salt thereof.

A preferred method for preparation of the compounds of formula I involves in a Step A reaction the nitration of the corresponding hydroxy compound of forumula II:

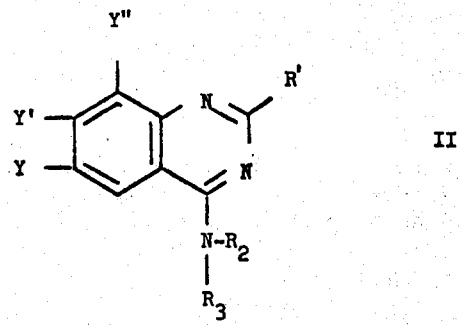

wherein Y, Y', Y'' and R' are as defined and $R_2$ and $R_3$ are the non-nitrate bearing hydroxyalkyl substituents corresponding to R and $R_1$, respectively, i.e.:

$R_2$ is from the group of:
  a. $-CH_2(-CH_2)_n-OH$ b. $-CH_2(-\overset{R_n}{\underset{|}{C}H})_n-OH$, and c. $-CH_2(-CH_2)_z-N[-CH_2(-CH_2)_y-OH]_2$ $R_3$ is from the group of:
  d. $-CH_2(-CH_2)_n-OH$ when $R_2$ is a) as above defined,
  e. hydrogen, and
  f. lower alkyl of 1 to 4 carbon atoms, $R_n^0$ is hydrogen, $-(CH_2-)_mCH_3$ or $-(CH_2-)_nOH$, provided that one $R_n^0$ is other than hydrogen, that the sum of n and m does not exceed 6 and that the sum of n and y does not exceed 7, or $R_2$ and $R_3$ together with the 4- amino nitrogen attached to the quinazoline ring form

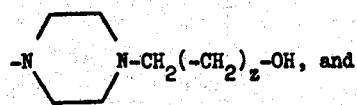

n, m, y and z and Y, Y' are as defined.

The preparation of compounds I by Step A involves a nitration reaction which may be carried out in a manner known per se for nitrating hydroxyalkyl groups. A preferred method of conducting the nitration involves thee reaction of a compound II with nitric acid in presence of a carboxylic acid anhydride which is preferably of from 3 to 8 carbon atoms, more preferably acetic acid anhydride. The reaction may be suitably carried out in an organic solvent medium at temperatures in the range of from minus 70°C. to plus 50°C., preferably minus 10°C. to plus 10°C. The solvent medium for the reaction is preferably provided by employing a lower aliphatic carboxylic acid, e.g., acetic acid, although other well known organic solvents may be employed or the reaction may be carried out employing an excess of the carboxylic acid anhydride. The product compound I may be isolated from the reaction mixture of Step A by working up by established procedures.

A preferred method for preparation of compounds II involves a Step B reaction of a 4-haloquinazoline of formula III:

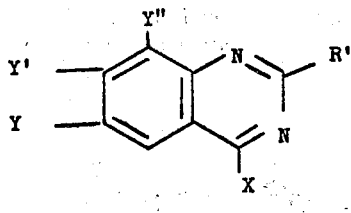

wherein Y, Y', Y'' and R' are as defined and X is halo from the group of chloro or bromo, preferably chloro, with a compound of formula IV:

wherein $R_2$ and $R_3$ are as defined.

The reaction of Step B is of known type and may be carried out in a conventional manner by subjecting a compound III to reaction with the compound IV at elevated temperatures which may be suitably in the range of minus 10°C. to 180°C., preferably 60°C. to 120°C. The reaction may be suitably carried out in an inert organic solvent which may be any of several other well-known conventional solvents, preferably an aromatic solvent such as benzene. Another preferred solvent is isopropanol. Alternately, the reaction may be initiated and/or carried out in the inert liquid medium provided by employing an excess of compound IV when the compound is liquid at the reaction temperature or by fusion of solid reactants. An acid binding agent such as sodium carbonate may be also employed to advantage in the reaction, if desired. The reaction product compound II may be isolated from the reaction mixture of Step B by established procedures.

The compounds of formulae III and IV are either known or may be prepared from known materials by established procedures, for example, as described in U.S. Letters Pat. No. 3,517,005.

Also within the scope of the novel compounds of the invention are pharmaceutically acceptable salts not materially affecting the pharmacological effect of the compounds of formula I. Such salts include the acid addition salts, e.g., the methane sulfonate, hydronitrate, hydrosulfate, fumarate, hydrochloride and maleate. It is convenient to prepare the compounds of formula I as a hydronitrate addition salt. Such salts may be then readily converted to the free bases by conventional procedures. In preparing the free bases from the acid addition salt, it is also convenient to employ a buffer system, e.g., a system comprising a 1:1 molar mixture of acetic acid and sodium acetate, followed by working up by conventional procedures. The free bases may be readily converted into the hydronitrate and other acid addition salts by established procedures.

The compounds of formulae I and II and their pharmaceutically acceptable acid addition salts are useful because they possess pharmacological activity in animals. In particular, the compounds of the formulae I and II are useful as antianginal agents as indicated by effecting coronary dilation in the anesthetized dog on intravenous administration and measurement of blood flow through the anterior descending branch of the left coronary artery.

Various of the compounds of the formula I, as represented particularly by the compounds of the formula Ia:

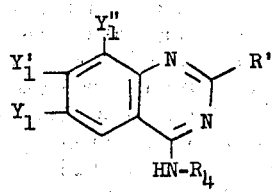

in which R' is as defined above, $Y_1$, $Y_1'$ and $Y_1''$ are alkoxy of 1 to 3 carbon atoms and $R_4$ is
$-CH_2(-CH_2)_p-ONO_2$
in which p is 4 to 6, preferably 4 or 5, are also useful as anti-arrythmic agents, as indicated by polygraph recordings on intravenous administration to the anesthetized dog given Ouabain until the appearance of constantly occuring ventricular ectopic beats and then the test compound every two minutes until the arrhythmia reverts to sinus rhythm.

For the above uses, the compounds of the formulae I and II may be combined with a pharmaceutically acceptable carrier, and such other conventional adjuvants as may be necessary, and administered orally in such forms as tablets, capsules, elixirs, suspensions and the like or parenterally in the form of an injectable solution or suspension. For the above-mentioned uses, the dosage administered will, of course, vary depending upon the compounds used, the therapy desired and the mode of administration. However, for use as antiarrhythmic agents, satisfactory results in general are obtained with the compounds of the formula Ia when administered at a daily dosage of from about 0.01 milligrams to about 100 milligrams per kilogram of body weight, preferably given in divided doses 2 to 4 times a day, or in sustained release form. For most larger mammals, the administration of from about 16 milligrams to about 1000 milligrams of the compound per day provides satisfactory results and dosage forms suitable for internal administration comprise from about 4 milligrams to about 500 milligrams of the compound in admixture with a solid or liquid pharmaceutical carrier or diluent.

As anti-anginal agents, satisfactory results may be obtained with the compounds of the formulae I and II when administered at a daily dosage of from 0.01 to 100 milligrams per kilogram of body weight, given as required or in divided doses or in sustained release form. For most larger mammals a dosage of from 16 to 1000 milligrams, pro re nata, provides satisfactory results. The compounds may also be used prophylactically in mammals to prevent or minimize angina attacks at a daily dosage of 16 to 500 milligrams, or in divided doses of from 4 to 250 milligrams.

Certain of the compounds of the formulae I and II, i.e. those of the following formulae Ib, IIa, IIb and IIc:

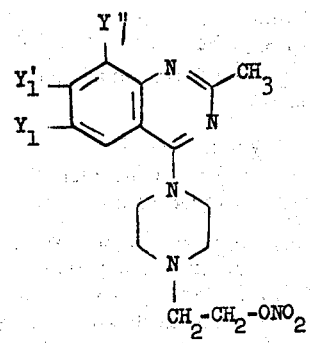

Ib

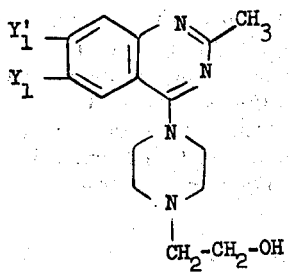

IIa

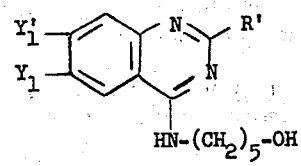

IIb

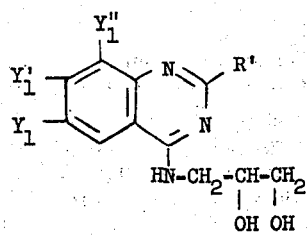

IIc wherein R', $Y_1$, $Y_1'$, and $Y_1''$ are as defined above, are also useful as agents in the treatment of myocardial shock (positive inotropic effect) as indicated on intravenous administration (0.5 to 20 milligrams per kilogram) to the anesthetized dog and measuring the myocardial contractile force with a Walton Brodie strain gauge.

For the treatment of myocardial or hemorrhagic shock the compounds of the formulae Ib, IIa, IIb and IIc may be effectively administered at a dosage of from 0.0001 to 40 milligrams per kilogram of animal body weight, pro re nata. For most mammals satisfactory results are obtained on the administration of from 0.01 to 50 milligrams, pro re nata. For this usage the compounds are preferably administered parenterally, e.g., intravenously.

Preferred compounds from the standpoint of antiarrhythmic activity are those of Examples 2 (e–1), 2 (i–1) and 2 (h–1) hereinafter.

Preferred compounds from the standpoint of use in the treatment of myocardial shock are those of Examples 1 (Step A), 2 (d), 2 (k) and 2 (c–1) hereinafter.

The compounds of the formula II also form acid addition salts and those pharmaceutically acceptable acid salts of the compound of the formula II are included within the scope of the pharmaceutically useful compounds of the formula II of the invention. Such salts include by way of illustration the hydrochloride, maleate and methanesulfonate and may be formed from or converted to the corresponding free base by conventional procedures.

For the above usages, oral administration with carriers may take place in such conventional forms as tablests, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, i.e., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. Except for the use in the treatment of shocks the preferred pharmaceutical compositions from the standpoint of preparation and ease of administration are solid compositions, particularly hard-filled gelatin capsules and tablets.

A representative formulation is a tablet prepared by conventional tabletting techniques and containing the following ingredients:

| Ingredients | Weight (mg.) |
| --- | --- |
| Compound of the formula I | 50 |
| Tragacanth | 10 |
| Lactose | 197.5 |
| Corn starch | 25 |
| Talcum | 15 |
| Magnesium stearate | 2.5 |

Compositions for parenteral administration for use, for example, in the treatment of shocks, may be formulated by well-known methods to contain an effective amount of the active ingredient of the invention in a conventional inert carrier or suspension or solvent medium, together with other additives such as dispersing agents, wetting agents, buffering agents and other conventional ingredients, as desired.

A representative formulation for intravenous administration for treatment of myocardial shock is a solution prepared by standard procedures and containing the following ingredients:

| Ingredient | Weight (%) |
|---|---|
| Compound of Step A of Example 1 | 5 (5 milligrams) |
| Sodium chloride | to make isotonic |
| Buffer Agent | to adjust pH |
| Ethanol, U.S.P. | 10–20 |
| Propylene Glycol | 15–25 |
| Water for Injection | 55–75 |

In general, the compositions of the invention adapted for either oral or parenteral administration may contain 1% to 90% by weight of the active ingredient in combination with the inert carrier, more usually 3% to 40%.

The following examples are given for the purpose of illustration only.

EXAMPLE 1

4-[4-(2-hydroxyethyl)-1-piperazino]-2-methyl-6,7-dimethoxyquinazoline nitrate

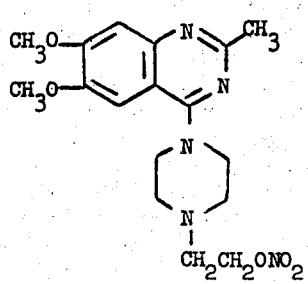

STEP A: Preparation of 4-[4-[4-(2-hydroxyethyl-1-piperazino]-2-methyl-6,7-dimethoxyquinazoline.

A mixture of 4.76 g. of 4-chloro-6,7-dimethoxyquinazoline and 2.86 g. of 2-hydroxyethylpiperazine is refluxed one-half hour along with 5 ml. of isopropanol and 3.2 g. of sodium carbonate. The resulting mixture is treated by addition of methanol and then heated to redissolve the reaction product. The reaction mixture is then filtered and then evaporated in vacuo to remove methanol. The resulting product is then purified by chromatography on 50 g. silica gel using chloroform as eluant to obtain 4-[4-(2-hydroxyethyl)-1-piperazino]-2-methyl-6,7-dimethoxyquinazoline, m.p. 156.5°–158°C.

The free base above obtained in an amount of 2.0 g. is treated in methanol with hydrogen chloride to obtain a dihydrochloride salt which was redissolved with water followed by treatment with charcoal and evaporation in vacuo to a minimum volume. The residue was treated with isopropanol to obtain 4-[4-(2-hydroxyethyl-1-piperazino]-2-methyl-6,7-dimethoxyquinazoline dihydrochloride monohydrate.

STEP B: Preparation of 4-[4-(2-hydroxyethyl)-1-piperazino]-2-methyl-6,7-dimethoxyquinazoline nitrate.

A solution of 2.69 g. of 4-[4-(2-hydroxyethyl)-1-piperazino]-2-methyl-6,7-dimethoxyquinazoline in 5 ml. of glacial acetic acid is added dropwise to a stirred mixture of 11.2 ml. of acetic anhydride and 3.72 ml. of 90% nitric acid at a tempperature of minus 2°C. to 0°C. The resulting mixture is stirred for 1 hour and then added to an excess of ice-cold aqueous ammonia solution. The resulting mixture is treated by addition of diethyl ether and filtered to obtain the Title compound as the dihydronitrate salt, m.p. 157°C. (decomp.). The dihydronitrate salt is suspended in 100 ml. of cold water and treated with 5 ml. of concentrated ammonia followed by extraction with chloroform. The extract is then filtered through 100 ml. of silica gel using chloroform to obtain 4-[4-(2-hydroxyethyl)-1-piperazino]-2-methyl-6,7-dimethoxyquinazoline nitrate, m.p. 127.5–129°C. (decomp.).

EXAMPLE 2

Following the procedure of Example 1 the following compounds are similarly prepared:

a. 4-[3-bis(2-hydroxyethyl)aminopropyl]amino-2-methyl-6,7-dimethoxyquinazoline, m.p. 144.5°–147°C.

a-1. 4-[3-bis(2-hydroxyethyl)aminopropyl]amino-2-methyl-6,7-dimethoxyquinazoline dinitrate, m.p. 77.5°–79.5°C.

b. 4-[3-bis(2-hydroxyethyl)aminopropyl]amino-2-methyl-6,7,8-trimethoxyquinazoline, m.p. 103.5°–105°C.

b-1. 4-[3-bis(2-hydroxethyl)aminopropyl)amino-2-methyl-6,7,8-trimethoxyquinazoline dinitrate dihydrochloride, m.p. 117°–119°C. (decomp.).

c. 4-[4-(2-hydroxyethyl)-1-piperazino]-2-methyl-6,7,8-trimethoxyquinazoline, m.p. 127°–128.5°C.

c-1. 4-[4-(2-hydroxyethyl)-1-piperazino]-2-methyl-6,7,8-trimethoxyquinazoline nitrate dihydronitrate, m.p. 139°C. (decomp.).

d. 4-(5-hydroxypentyl)amino-2-methyl-6,7-dimethoxyquinazoline, m.p. 140°–141.5°C.

d-1. 4-(5-hydroxypentyl)amino-2-methyl-6,7-dimethoxyquinazoline nitrate, m.p. 135.5°–137°C.

e. 4-(5-hydroxypentyl)amino-2-methyl-6,7,8-trimethoxyquinazoline, m.p. 91–93.5°C.

e-1. 4-(5-hydroxypentyl)amino-2-methyl-6,7,8-trimethoxyquinazoline nitrate hydronitrate, m.p. 86.5°–87.5°C.

f. 4-(4-hydroxybutyl)amino-2-isopropyl-6,7,8-trimethoxyquinazoline, m.p. 139°C.

f-1. 4-(4-hydroxybutyl)amino-2-isopropyl-6,7,8-trimethoxyquinazoline nitrate, m.p. 83°C.

g. 4-(5-hydroxypentyl)amino-2-ethyl-6,7,8-trimethoxyquinazoline, m.p. 86°C.

g-1. 4-(5-hydroxypentyl)amino-2-ethyl-6,7,8-trimethoxyquinazoline nitrate.

h. 4-(5-hydroxypentyl)amino-2-isopropyl-6,7,8-trimethoxyquinazoline, m.p. 112°C.

h-1. 4-(5-hydroxypentyl)amino-2-isopropyl-6,7,8-trimethoxyquinazoline nitrate, m.p. 89°C.

i. 4-(6-hydroxyhexyl)amino-2-methyl-6,7,8-trimethoxyquinazoline maleate, m.p. 120°C.

i-1. 4-(6-hydroxyhexyl)amino-2-methyl-6,7,8-trimethoxyquinazoline nitrate in 1⅛ hydronitrate form, m.p. 97°–99°C.

j. 4-(6-hydroxyhexyl)amino-2-isopropyl-6,7,8-trimethoxyquinazoline.

j-1. 4-(6-hydroxyhexyl)amino-2-isopropyl-6,7,8-trimethoxyquinazoline nitrate, m.p. 99°C.

k. 4-(2,3-dihydroxypropyl)amino-2-methyl-6,7,8-trimethoxyquinazoline, m.p. 95°C.

k-1. 4-(2,3-dihydroxypropyl)amino-2-methyl-6,7,8-trimethoxyquinazoline dinitrate, m.p. 166°C (decomp.).

l. 4-[4-(2-hydroxyethyl)-1-piperazino-2-isopropyl-6,7,8-trimethoxyquinazoline dimaleate, m.p. 125°C.

l-1 4-[4-(2-hydroxyethyl)-1-piperazino-2-isopropyl-6,7,8-trimethoxyquinazoline nitrate fumarate.

m. 4-[4-(2-hydroxyethyl)-1-piperazino]-2-ethyl-6,7,8-trimethoxyquinazoline dimaleate, m.p. 127°C.

m-1. 4-[4-(2-hydroxyethyl)-1-piperazino]-2-ethyl-6,7,8-trimethoxyquinazoline nitrate.

n. 4-[4-(3-hydroxypropyl)-1-piperazino]-2-methyl-6,7-dimethoxyquinazoline dihydrochloride hydrate, m.p. 235°C. (decomp.).

n-1. 4-[4-(3-hydroxypropyl)-1-piperazino]-2-methyl-6,7-dimethoxyquinazoline nitrate.

o. 4-[4-(4-hydroxybutyl)-1-piperazino]-2-methyl-6,7-dimethoxyquinazoline dihydrochloride hydrate, m.p. 226°–227°C. (decomp.).

o-1. 4-[4-(4-hydroxybutyl)-1-piperazino]-2-methyl-6,7-dimethoxyquinazoline nitrate.

What is claimeed is:

1. The method of treating myocardial shock comprising administering to a mammal in need of such treatment a myocardial shock treating effective amount of a compound selected from the group consisting of compounds of the formulae:

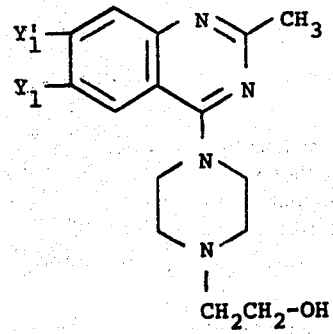

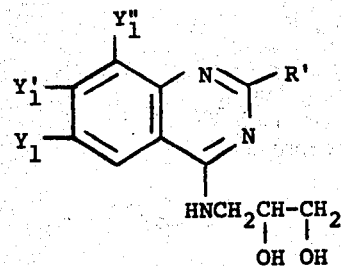

and

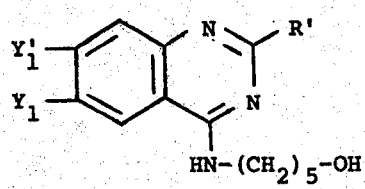

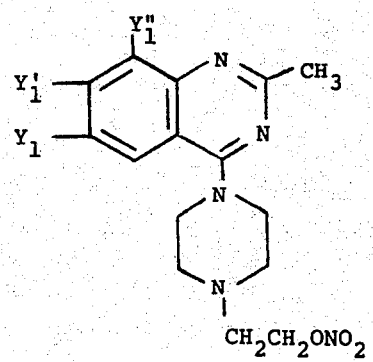

wherein R' is alkyl of 1 to 4 carbon atoms, and each of $Y_1$, and $Y_1'$ and $Y_1''$ is alkoxy of 1 to 3 carbon atoms, or a pharmaceutically acceptable non-toxic acid addition salt thereof.

2. The method of claim 1 in which the compound is of the formula:

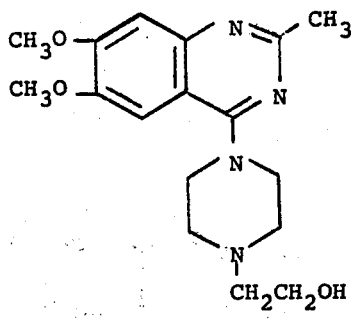

or a pharmaceutically acceptable non-toxic acid addition salt thereof.

3. The method of claim 1 in which the compound is of the formula:

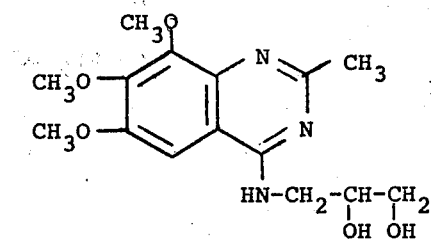

or a pharmaceutically acceptable non-toxic acid addition salt thereof.

4. The method of claim 1 in which the compound is of the formula:

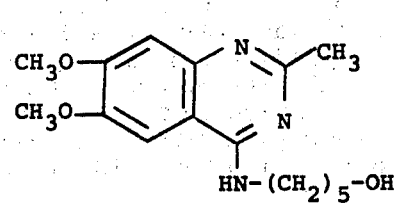

or a pharmaceutically acceptable non-toxic acid addition salt thereof.

5. The method of claim 1 in which the compound is of the formula:

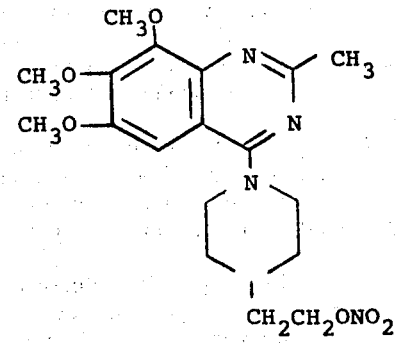

or a pharmaceutically acceptable non-toxic acid addition salt thereof.

* * * * *